US012457677B2

(12) United States Patent
Hassfurter et al.

(10) Patent No.: US 12,457,677 B2
(45) Date of Patent: Oct. 28, 2025

(54) PLASMA DEVICE

(71) Applicant: BSH Hausgeräte GmbH, Munich (DE)

(72) Inventors: Stefan Hassfurter, Maroldsweisach (DE); Tobias Wende, Prien (DE); Julius Geis, Burkardroth (DE)

(73) Assignee: BSH Hausgeräte GmbH, Munich (DE)

( * ) Notice: Subject to any disclaimer, the term of this patent is extended or adjusted under 35 U.S.C. 154(b) by 267 days.

(21) Appl. No.: 18/255,414

(22) PCT Filed: Nov. 16, 2021

(86) PCT No.: PCT/EP2021/081796

§ 371 (c)(1),
(2) Date: Jun. 1, 2023

(87) PCT Pub. No.: WO2022/117329

PCT Pub. Date: Jun. 9, 2022

(65) Prior Publication Data

US 2024/0098868 A1 Mar. 21, 2024

(30) Foreign Application Priority Data

Dec. 1, 2020 (DE) ..................... 10 2020 215 112.1

(51) Int. Cl.
*A61L 2/14* (2006.01)
*D06M 10/02* (2006.01)
*H05H 1/24* (2006.01)

(52) U.S. Cl.
CPC ................. *H05H 1/24* (2013.01); *A61L 2/14* (2013.01); *D06M 10/025* (2013.01);
(Continued)

(58) Field of Classification Search
CPC .. H05H 1/24; H05H 2245/36; H05H 2245/40; H05H 2245/60; A61L 2/14; A61L 2202/16; A61L 2202/26; D06M 10/025
See application file for complete search history.

(56) References Cited

U.S. PATENT DOCUMENTS 8,810,134 B2 * 8/2014 Watson .................... H05H 1/46
315/111.41
10,300,159 B2 5/2019 Morfill et al.
(Continued)

FOREIGN PATENT DOCUMENTS

CN 205814739 U 12/2016
CN 108771767 A 11/2018
(Continued)

OTHER PUBLICATIONS

Machine Translation of DE102018213144A1. (Year: 2020).*

*Primary Examiner* — Alexander H Taningco
*Assistant Examiner* — Pedro C Fernandez
(74) *Attorney, Agent, or Firm* — Laurence A. Greenberg; Werner H. Stemer; Ralph E. Locher

(57) ABSTRACT

A plasma device for treating surfaces, in particular surfaces of fabrics. In order to allow for better ease of handling, an elongate housing is provided which can be manipulated with one hand and in which a plasma source is arranged. The plasma source has a plateau surface that extends in the longitudinal direction of the housing and includes at least one electrode via which plasma can be dispensed onto the surface to be treated. A center of gravity M and a geometrical center G are located at a distance of less than 20 mm from one another.

19 Claims, 2 Drawing Sheets

(52) U.S. Cl.
CPC ....... *A61L 2202/16* (2013.01); *A61L 2202/26* (2013.01); *H05H 2245/36* (2021.05); *H05H 2245/40* (2021.05); *H05H 2245/60* (2021.05)

(56) References Cited

U.S. PATENT DOCUMENTS

| | | | | |
|---|---|---|---|---|
| 11,337,295 | B2 | 5/2022 | Nettesheim et al. | |
| 2017/0095050 | A1 | 4/2017 | Dineen | |
| 2021/0290799 | A1* | 9/2021 | Zhong | A61L 2/14 |
| 2024/0173445 | A1* | 5/2024 | An | A61L 2/14 |

FOREIGN PATENT DOCUMENTS

| | | | |
|---|---|---|---|
| DE | 102011100751 | A1 | 11/2012 |
| DE | 102018213143 | A1 | 2/2020 |
| DE | 102018213144 | A1 * | 2/2020 |
| DE | 202018006360 | U1 | 2/2020 |
| DE | 102019107238 | A1 | 9/2020 |
| JP | 2013254593 | A | 12/2013 |

* cited by examiner

PLASMA DEVICE

FIELD AND BACKGROUND OF THE INVENTION

The present invention relates to a plasma device for treating surfaces, in particular of fabrics.

DE 10 2011 100 751 A1 discloses a generic plasma device for inactivating preferably odor-relevant molecules and thus for freshening up surfaces, for instance of fabrics. The plasma device has a housing and an associated plasma source and at least one spacer, which ensures that a predefined distance is retained between the plasma source and a surface to be treated, with which molecules accumulating on the surface to be treated can be inactivated by means of electrons of the plasma.

A quick cleaning of surfaces, for instance textiles, is however not always possible by means of washing or cleaning, with the result that plasma devices are used herefor for instance, by means of which bacteria, germs, viruses, spores, fungi and odor molecules can in particular be inactivated.

CN 205 814 739 U discloses a portable sterilization and disinfection machine, with a housing, an energy storage device, which is arranged in the housing, and with a transformer. An output voltage of the energy storage device is amplified here and configured by way of the transformer such that with it ozone and negative ions can be generated by high voltage discharge under the amplification voltage output by the transformer.

CN 108 771 767 A discloses a cleaning device for cleaning clothing, having a housing in which a receiving space for receiving a fan is provided. Similarly, a separator is provided in the receiving space, said separator separating an air inlet region from a cleaning region. Here the cited regions are arranged vertically one above the other in the operating state. The items of clothing to be treated can be freed or cleaned in particular of cigarette smoke using the cleaning device.

The disadvantage with devices known from the prior art is often that these become heavy and uncomfortable in a user's hand particularly during prolonged use and as a result negatively impact ease of use.

SUMMARY OF THE INVENTION

The present invention therefore deals with the problem of specifying an improved or at least an alternative embodiment for a plasma device of the generic type, which overcomes in particular the disadvantages known from the prior art.

This problem is achieved in accordance with the invention by the subject matter as claimed. Advantageous embodiments form the subject matter of the dependent claims.

The present invention is based on the general idea of embodying a plasma device, to be operated using one hand, for treating surfaces, in particular for freshening up textiles, which can be designed in particular as a textile treatment plasma device, so that this can be comfortably used with one hand over the long term by a specific ratio of a center of mass M in relation to a geometrical center G, in other words in relation to a volume center, being predetermined. The inventive plasma device here has an elongate housing which can be operated with one hand and which can be gripped by a hand of a user in a simple and form-fit manner. A plasma source is arranged in the housing, said plasma source having a plateau surface which extends in the longitudinal direction of the housing and has at least one electrode, for instance a slightly raised electrode with a ceramic substrate surrounding the same, by way of which plasma can be produced and can be applied to the surface to be treated, for instance to the textile to be freshened up. In accordance with the invention, a center of gravity M and a geometrical center G now have a distance A of less than 20 mm. On account of the inventively restricted distance A between the center of mass M and the geometrical center G, in other words between the center of gravity M and volume center, the hand-guided plasma device can move, lift and tilt easily, since only extremely minimal torques occur during tilting, rotating etc. A pushing movement of a user's hand in the activation direction can moreover be supported by means of the inventive arrangement of the center of gravity M. The elongate housing here has a cross-sectionally essentially oval design and is thus optimally adjusted to the palm of a hand. In order in the process to be able to comfortably design operation equally both for a right-handed person and also for a left-handed person, the inventive plasma device or its housing can be embodied symmetrically with respect to a longitudinal center plane or transverse center plane. On account of the inventively predetermined maximum distance A between the center of gravity M and geometrical center G of less than 20 mm, it is moreover possible to achieve extremely pleasing ergonomics and thus easy and comfortable operability of the plasma device.

In addition to the three physical states, solid, liquid or gas, plasma is referred to as the fourth physical state. If sufficient energy is fed to a gas or gas mixture in the form of electrical energy, for instance, a few atoms of the gas are therefore ionized, i.e. electrons are removed from the atom sleeve and move as free particles so that a positively charged atom remains. If a gas consists of a sufficiently high portion of free ions and electrons, the physical state is referred to as plasma. Plasma is therefore material, the component parts of which are in part charged components, ions and electrons, which move as free charge carriers.

Non-thermal plasma, which is also referred to as cold plasma, can be used deliberately to eliminate odors and specific hydrocarbons. Furthermore, non-thermal plasmas are used in medical technology, for instance when treating poorly-healing or non-healing wounds with the aid of a so-called plasma pen, by reverting to the antimicrobial effect of "cold plasma".

The causes of the antibacterial effect of a plasma lie in heat, drying, shear stress, UV radiation, free radicals and charges. With cold plasmas, such as are used in the inventive plasma device, heat plays a subordinate role, since these plasmas are operated at room temperature. In such low pressure plasmas, particularly reactive particles develop, such as for instance different oxygen or nitrogen species, which have a sufficiently high service life in order to damage organic compounds with an indirect exposition. Atomic oxygen, superoxide radicals, ozone, hydroxyl radicals, nitrogen monoxide and nitrogen dioxide form part of these particles. These particles indicate a damaging effect on different odor components such as also cell components. If odor components, which mostly consist of carbon compounds, such as also cell walls of bacteria, germs, viruses, fungi or other comparable microorganisms, are exposed to the plasma directly, these can charge negatively on account of the bombardment with the electrons present in the plasma. On account of the electrostatic repulsion, this results in mechanical stresses to the point of exceeding the tensile strength and the destruction of the odor molecule, or the cell wall. However, it is not only mechanical tensionings on account of the charge that can damage the cell walls, but instead also the interference in the charge equilibrium of the odor molecules or of the cell wall as a result of different, further electrostatic effects and the electrolysis, e.g. by changing the permeability of the cell walls. A mechanism for inactivating microorganisms is also produced from the very energy-rich ions. The plasma can be generated by means of a high frequency. Low pressure plasmas are therefore particularly well suited to inactivating odors on textile fabric or on common household surfaces or such like, in order to achieve odor inactivation.

Here the surfaces to be treated can be textile materials with natural, plant or animal fibers, such as e.g. cotton, sheep wool, silk, linen, felt or artificial fibers, such as e.g. nylon. The term "surface" should also be understood to mean materials and objects made from ceramic, plastic, feather, leather, glass, wood or metal.

The odor-relevant molecules which can be neutralized with the inventive plasma device can be butyric acid, sweat, ingrained cigarette smoke or general odors, which can be perceived to be unpleasant. The plasma device is based on the odors being actively eliminated and malodor odors not being concealed by means of perfume, for instance. Non odor-relevant molecules, such as allergens, protein molecules, prions etc. for instance can also be destroyed using the inventive plasma device.

In an advantageous development of the inventive solution, the center of gravity M and the geometrical center G have a distance A of less than 10 mm, in particular a distance A of less than 5 mm. This makes it possible to move the center of gravity M and the geometrical center G increasingly toward one another, as a result of which less force is increasingly required for lifting, rotating and tilting and an increasingly more comfortable use of the inventive plasma device is given as a result. An inventive plasma device represents the ideal case here, in which the center of gravity M and the geometrical center G are identical. This ensures a particularly ergonomic and pleasant use of the plasma device.

Expediently, a geometrical longitudinal axis of the plasma device intersects a first circular surface with a radius $R_1 \leq 5$ mm, wherein the center of gravity M forms a center point of this first circular surface. In this way it is possible to ensure that even with an eccentric pressing of the plasma device against the surface to be treated, a reliable movement of the plasma device and activation of the plasma source can be ensured. In an embodiment of this type, it is therefore possible to ensure that a reliable activation of the plasma source and thus a reliable treatment, in particular freshening up, of surfaces to be treated, in particular textiles, can also take place with the very different top or pressure angles.

In a further advantageous embodiment of the inventive solution, a geometrical transverse axis of the plasma device intersects a second circular surface with a radius $R_2 \leq 5$ mm, wherein the center of gravity M forms a center point of this second circular surface. In addition or alternatively, provision can be made for a geometrical vertical axis of the plasma device to intersect a third circular surface with a radius $R_3 \leq 5$ mm, wherein the center of gravity M forms a center point of this third circular surface. Even with a restriction of the radius of the third or second circular surface of this type by a geometrical vertical axis or geometrical transverse axis, it is possible to ensure that with an eccentric pressing of the plasma device on the surface to be treated, for instance on the textile to be treated, the plasma source can be reliably activated. Ideally the longitudinal axis, the transverse axis and the vertical axis of the plasma device intersects a ball with a radius of $R_K \leq 5$ mm, wherein the center of gravity M of the plasma device represents the center point of the ball. In this way it is possible for a user to move, in particular tilt, yaw or roll the hand-guided plasma device with minimal effort. In concrete terms, this means that when the plasma device is positioned in the space, only minimal torques to be applied are required, so that the inventive plasma device can also be easily guided to points in the surfaces to be treated which are difficult to access, for instance in the textiles to be treated, but also under a person's armpits.

The plasma device is expediently embodied symmetrically about at least the longitudinal axis, the transverse axis or the vertical axis. This offers the large advantage that the plasma device can be easily gripped by way of its housing and is easy in respect of handling, in particular also in respect of movement.

A switch for switching the inventive plasma device on and off is expediently provided, wherein the center of gravity M and the switch are arranged offset with respect to the geometrical center. On account of the inventively arranged center of gravity M, an intuitive grasping of the plasma device is facilitated to a user, wherein the center of gravity M preferably lies in the palm of a hand and the switch can be easily operated with an index finger. Moreover, an arrangement of the center of gravity M of this type and of the diametrically opposing switch facilitates operation of the inventive plasma device both by means of left-handed and also right-handed people and overall a simple and comfortable one-handed operation/use.

The plasma source is expediently spring-loaded and protrudes beyond the housing in a non-use state of the plasma device. A spring-loading of the plasma source makes it possible to guide the plateau surface closely toward the surface during the cleaning process, as a result of which in particular excessive ozone production by the plasma source can be prevented. The spring-loaded plateau surface also brings about a shielding of the emitted plasma from atmospheric oxygen, so that sufficient oxygen is then available for ozone production, the previously cited excessive ozone production does not take place with the disadvantages associated herewith. The disadvantages of excessive ozone production lie in particular in a longer effect on the surface to be treated, for instance a textile, in a discoloration of the same and in the risk of airway irritations.

Further important features and advantages of the invention become apparent from the subclaims, from the drawings and from the associated description of the figures using the drawings.

It is apparent that the previously cited features which are also still to be explained below can be used not only in the respectively specified combination, but also in other combinations or alone without departing from the scope of the present invention.

Preferred exemplary embodiments of the invention are shown in the drawings and are explained in more detail in the description below, wherein the same reference characters relate to identical or similar or functionally identical components.

BRIEF DESCRIPTION OF THE FIGURES

The drawings show, schematically in each case.

DETAILED DESCRIPTION OF THE INVENTION

Figure 1:
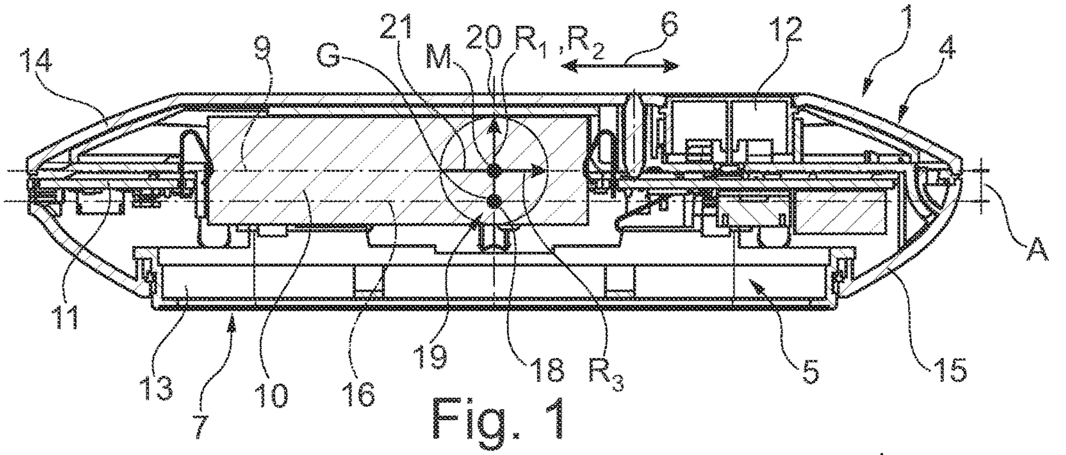
FIG. 1 a longitudinal sectional representation through an inventive plasma device, FIG. 2 a view from above onto the inventive plasma device, FIG. 3 a cross-sectional representation through the plasma device in a hand of a user in a non-use position, FIG. 4 a representation as in FIG. 3 but in a position of use, FIG. 5 a view from above onto an inventive plasma device during use.

According to FIG. 1 to 5, an inventive plasma device 1 for treating surfaces 2, in particular for treating textiles 3 (cf. FIG. 4) has an elongate and cross-sectionally oval-shaped housing 4, in which a plasma source 5 is arranged, which has a plateau surface 7, which extends in the longitudinal direction 6 of the housing 4, with at least one electrode 8, by way of which the plasma can be applied to the surface 2 to be treated. In order now to enable as comfortable and moreover easy operation or use of the inventive plasma device 1 as possible, provision is made for a center of gravity M and a geometrical center G to have a distance A of less than 20 mm. The center of gravity M and the geometrical center G very preferably have a distance A of less than 10 mm, in particular a distance A of less than 5 mm.

The center of gravity M is understood to mean the point of a body, here the plasma device 1, in which the entire mass can be considered to be combined. When the body is supported in the center of gravity M, the body remains at equilibrium. The geometrical center G corresponds here to the center of gravity of a body, which consists of homogeneous material, in other words has the same density overall. Different arrangements of individual components, such as shown in the present plasma device 1, but also different density ratios, can result in the center of gravity M and the geometrical center G, often also called volume center, not being identical. In order however to be able to guarantee as comfortable handling of the plasma device 1 as possible, attempts are made to arrange the center of gravity M and the geometrical center G as far as possible as close as possible next to one another, wherein ideally the geometrical center G and the center of gravity M are identical.

The center of gravity M of the plasma device 1 is moreover to lie as centrally as possible in respect of the plasma device 1 in an axis of rotation of a forearm of a user. Here a centerline 9 of the plasma device 1 should lie as close as possible to the palm of one's hand and moreover be at right angles to the axis of rotation of the forearm when the arm is extended.

In under to be able to arrange the geometrical center G and the center of gravity M at the smallest possible distance A from one another, individual components of the plasma device 1, such as for instance an energy storage unit 10, a main printed circuit board 11, the plasma source 5, a switch 12 and a holding frame 13 for the plasma source 5 must be arranged accordingly or adjusted with respect it their weight.

The housing 4 typically has a housing upper part 14 and a housing lower part 15 which are connected to one another by way of a clip connection, for instance. There is an opening in the base of the housing lower part 15, through which the plasma source 5 projects outwards from the housing 4.

A tipping of a movable plasma source 5 can in particular also be prevented by as close an arrangement of the center of gravity M and the geometrical center G as possible, even when the plasma device 1 is pressed eccentrically. A comparatively small distance A between the center of gravity M and the geometrical center G also makes it possible to achieve easy handling of the plasma device 1 in respect of a movement onto the surface 2 to be treated, as a result of which usage of the plasma device 1 is possible with minimal effort. Moreover, a rotation, tilting, tipping, rolling etc. of the plasma device 1 can take place without any large torques to be applied, so that this can also be easily guided to inaccessible points, for instance on the body under the armpit.

The plasma source 5 can moreover be spring-loaded and in a non-use state (cf. FIG. 3) project downward beyond the housing 4, and in a use state (cf. FIG. 4) be impressed at least partially into the housing 5, and as a result rest with the plateau surface 7 in a planar manner on the surface 2 to be treated. In this way, with a movement of the plasma device 1, it is also possible to ensure a uniform surface contact, as a result of which the plasma emitted by the plasma source 5 for treating the surface 2 does not come into contact with the ambient air and as a result less ozone which could result in a discoloration of the same when there is a prolonged effect on the surface 2 to be treated, for instance a textile 3, is also produced. The risk of airway irritation can also be reduced in this way.

Figure 2:
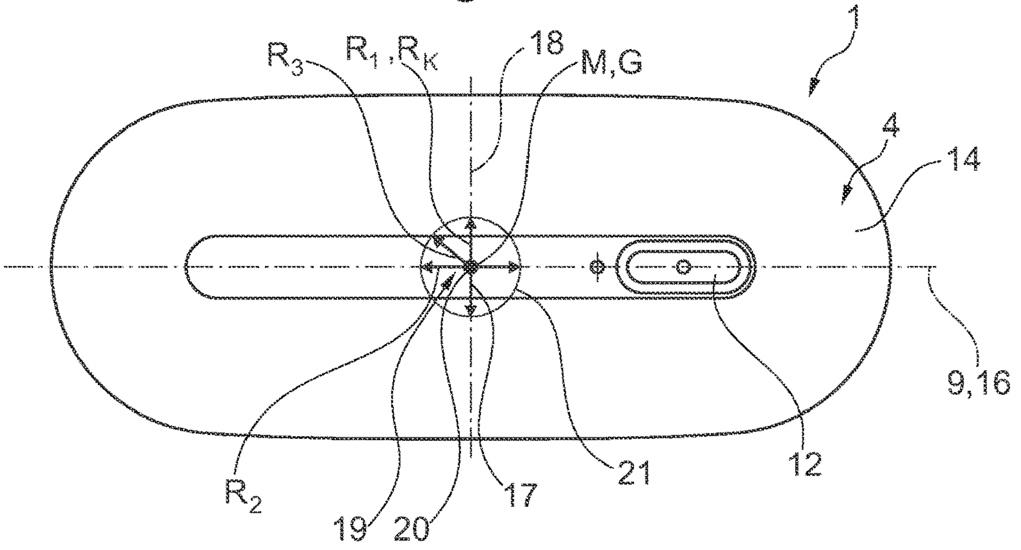
Figure 3:
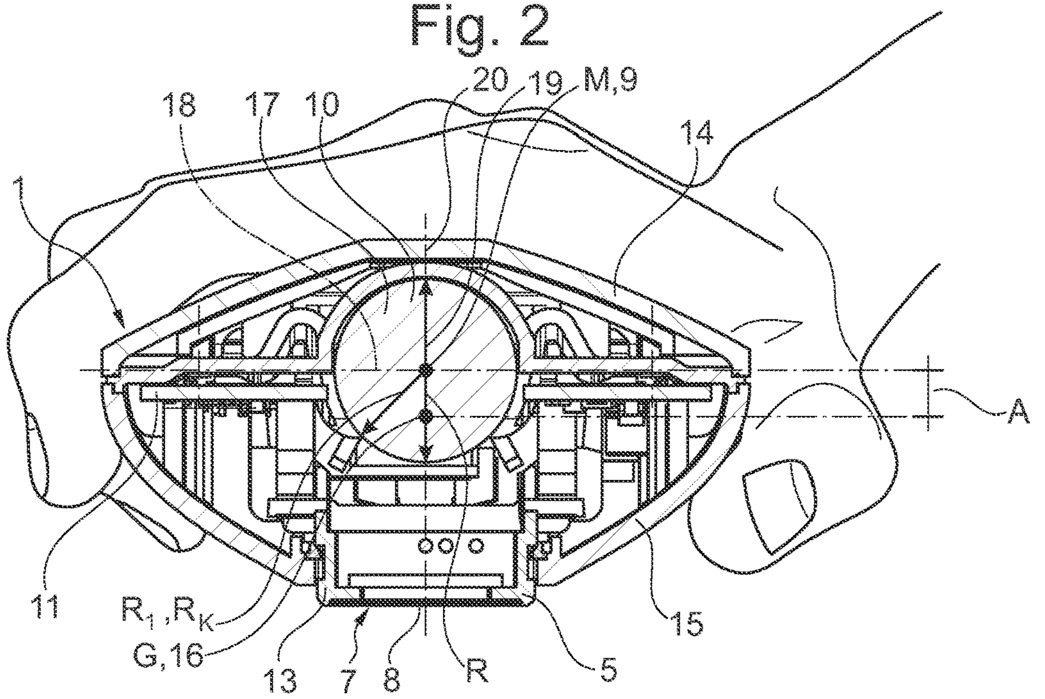

With an advantageous development of the inventive solution, a geometrical longitudinal axis 16 intersects a first circular surface 17 with a radius $R_1 \leq 5$ mm, wherein the center of gravity M forms a center point of the first circular surface 17. The first circular surface 17 runs here according to FIG. 1 orthogonally to the image plane and according to FIG. 3 in the image plane. According to FIG. 1, a centerline 9 runs here similarly to the geometrical longitudinal axis 16 horizontally in the image plane, wherein the center of gravity M lies on the centerline 9, while the geometrical center G lies on the geometrical longitudinal axis 16. In FIG. 2, the geometrical longitudinal axis 16 and the centerline 9 are arranged one behind the other in the image plane, in other words congruently. In FIG. 3, both the centerline 9 and also the geometrical longitudinal axis 16 run orthogonally to the center plane, while a geometrical transverse axis 18 and the geometrical vertical axis 20 run in the image plane.

Figure 4:
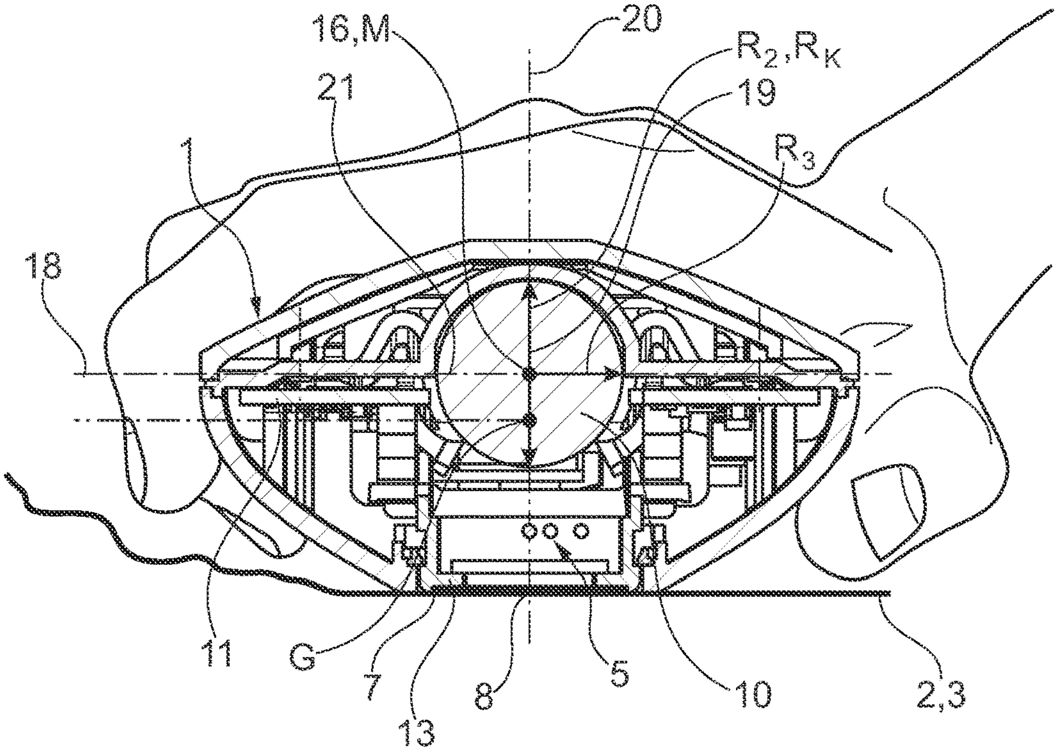
Figure 5:
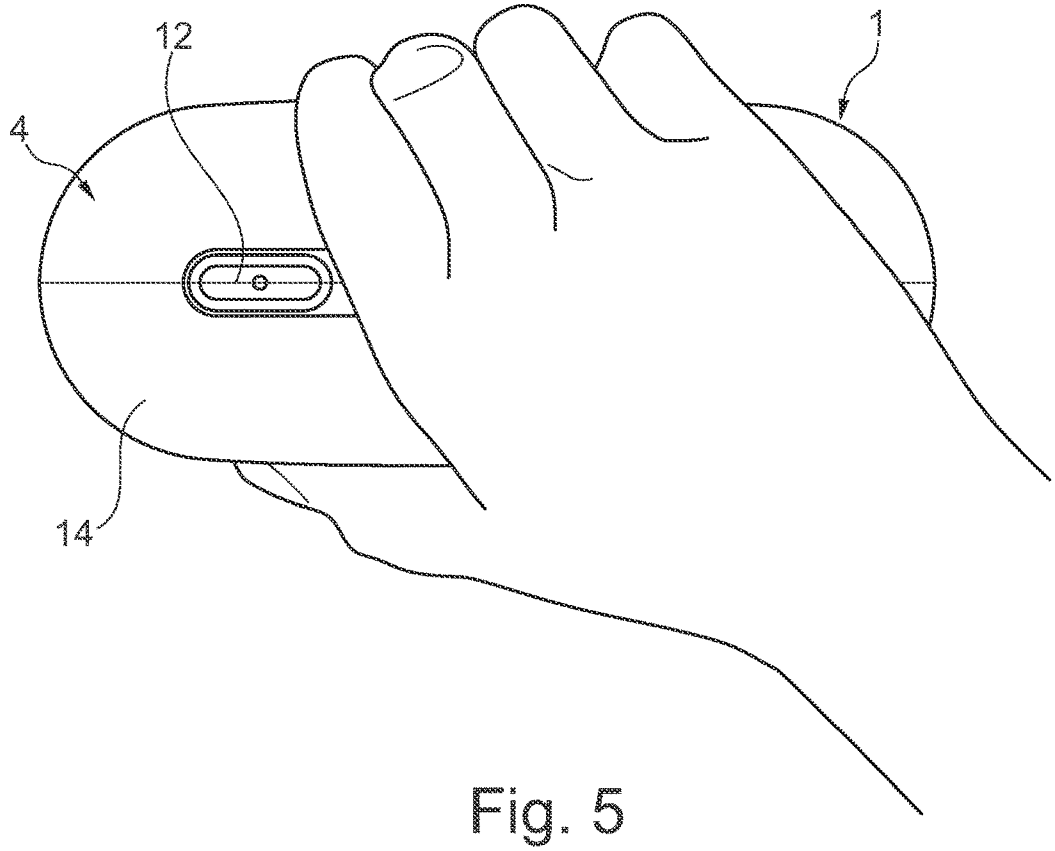

By observing FIGS. 1 and 4 further, it is possible to identify that the geometrical transverse axis 18 of the plasma device 1 intersects a second circular surface 19 with a radius $R_2 \leq 5$ mm, wherein the center of gravity M represents a center point of the second circular surface 19. The second circular surface 19 runs here according to FIG. 4 at right angles to the image plane and lies in the image plane in FIG. 1.

In a further advantageous embodiment of the inventive solution, a geometrical vertical axis 20, on which the geometrical center G lies, intersects a third circular surface 21 with a radius $R_3 \leq 5$ mm, wherein the center of gravity M forms a center point of the third circular surface 21. The third circular surface 21 runs here according to FIGS. 1, 3 and 4 horizontally in the image plane and according to FIG. in the image plane.

In a particularly preferred embodiment of the inventive plasma device 1, the geometrical longitudinal axis 16, the geometrical transverse axis 18 and the geometrical vertical axis 20 intersect a ball with a radius $R_K < 5$ mm, wherein the center of gravity M forms a center point of the ball. A ball of this type would be mounted here from the individual circular surfaces 17, 19 and 21.

The closest possible arrangement or identical arrangement of center of gravity and geometrical center G enables a comparatively simple rotation, rolling, pitching, tilting etc. of the plasma device 1 without larger torques, as a result of which a handling and usage of the inventive plasma device 1 can be designed comfortably by a user. The plasma device 1 can moreover be embodied symmetrically about at least the geometrical longitudinal axis 16, the geometrical transverse axis 18 or the geometrical vertical axis 20, in particular rotationally symmetrically, as a result of which the plasma device 1 can be gripped haptically easily. Simple handling of the same can also be achieved in this way.

Moreover, provision can be made for the switch 12 for switching the plasma device 1 on and off and the center of gravity M to be arranged offset with respect to the geometrical center G. The switch 12 can be in relation to the center M, S for instance. The switch 12 arranged offset can enable a simple activation or deactivation of the plasma device 1 by means of an index finger of the user, as a result of which an intuitive use is enabled.

On the whole, a comparatively simple and low-effort use of the same can be enabled with the inventive plasma device 1 and the preferably identical arrangement of the geometrical center G and the center of gravity M, as a result of which a significant increase in comfort in respect of the use can be achieved.

According to FIGS. 1, 3 and 4, the geometrical longitudinal axes 16 and the geometrical transverse axis 18 are arranged offset at distance A in each case with respect to the center of gravity M, wherein these can naturally also go through the center of gravity M.

LIST OF REFERENCE CHARACTERS

1 Plasma device
2 Surface
3 Textile
4 Housing
5 Plasma source
6 Longitudinal direction
7 Plateau surface
8 Electrode
9 Centerline
10 Energy storage unit
11 Main printed circuit board
12 Switch
13 Holding frame
14 Housing upper part
15 Housing lower part
16 Geometrical longitudinal axis
17 First circular surface
18 Geometrical transverse axis
19 Second circuit surface
20 Geometrical vertical axis
21 Third circular surface

The invention claimed is:

1. A plasma device for treating surfaces of fabrics, the plasma device comprising:
   - an elongate housing being formed to be operated with one hand;
   - a plasma source arranged in said housing, said plasma source having a plateau surface running in a longitudinal direction of said housing, said plateau surface having at least one electrode for producing a plasma to be applied to a surface to be treated;
   - the plasma device having a center of gravity M and a geometrical center G, and said center of gravity M and said geometrical center G are spaced by a distance A of less than 20 mm.

2. The plasma device according to claim 1, wherein said housing has a cross-section with an oval shape.

3. The plasma device according to claim 2, wherein said oval-shaped cross-section of said housing is adjusted to the palm of a hand to enable a hand of a user to grip said housing in a form-fit.

4. The plasma device according to claim 1, which comprises a holding frame for said plasma source with a given arrangement and/or with a given adjustment in respect of a weight thereof.

5. The plasma device according to claim 1, wherein the center of gravity M and the geometrical center G are disposed at a spacing distance A of less than 10 mm.

6. The plasma device according to claim 5, wherein the spacing distance A of less than 5 mm.

7. The plasma device according to claim 1, wherein the center of gravity M and the geometrical center G are identical.

8. The plasma device according to claim 1, wherein said plasma source is spring-loaded and in a non-use state of the plasma device projects beyond said housing and in a use state is impressed at least partially into said housing.

9. The plasma device according to claim 1, wherein a geometrical longitudinal axis of the plasma device intersects a first circular surface with a radius $R1 \leq 5.0$ mm, and wherein the center of gravity M forms a center point of the first circular surface.

10. The plasma device according to claim 9, wherein a geometrical transverse axis of the plasma device intersects a second circular surface with a radius $R2 \leq 5.0$ mm, and wherein the center of gravity M forms a center point of the second circular surface.

11. The plasma device according to claim 10, wherein a geometrical vertical axis of the plasma device intersects a third circular surface with a radius $R3 \leq 5.0$ mm, and wherein the center of gravity M forms a center point of the third circular surface.

12. The plasma device according to claim 11, wherein the geometrical longitudinal axis, the geometrical transverse axis, and the geometrical vertical axis of the plasma device intersect a ball with a radius $RK < 5.0$ mm, and wherein the center of gravity M forms a center point of the ball.

13. The plasma device according to claim 1, wherein a geometrical transverse axis of the plasma device intersects a circular surface with a radius $R2 \leq 5.0$ mm, and wherein the center of gravity M forms a center point of the circular surface.

14. The plasma device according to claim 1, wherein a geometrical vertical axis of the plasma device intersects a circular surface with a radius $R3 \leq 5.0$ mm, and wherein the center of gravity M forms a center point of the circular surface.

15. The plasma device according to claim 11, wherein the plasma device is embodied symmetrically about at least one of the geometrical longitudinal axis, the geometrical transverse axis or the geometrical vertical axis.

16. The plasma device according to claim 1, which comprises a switch for selectively switching the plasma device on and off, and wherein the center of gravity M and the switch are arranged offset with respect to the geometrical center G.

17. The plasma device for treating surfaces, the plasma device comprising:
   - an elongate housing configured to be operated with one hand, said housing having a housing upper part and a housing lower part;
   - a plasma source arranged in said housing, said plasma source having a plateau surface running in a longitudinal direction of said housing and having at least one electrode for generating a plasma to be applied to the surface to be treated;

wherein a center of gravity M of the plasma device and a geometrical center G of the plasma device are distanced from one another by a spacing distance A that is less than 20 mm; and wherein the center of gravity M is distanced from the geometrical center G in a direction of said housing upper part.

18. The plasma device according to claim 17 configured for treating surfaces of fabrics.

19. The plasma device according to claim 17, wherein said plasma source is spring-loaded and in a non-use state the plasma device projects beyond said housing and in a use state is impressed at least partially into said housing.

* * * * *